United States Patent
Miyamoto et al.

(10) Patent No.: US 8,647,650 B2
(45) Date of Patent: Feb. 11, 2014

(54) COMPOSITION FOR EXTERNAL USE AND METHOD FOR PRODUCING THE SAME

(75) Inventors: Masayoshi Miyamoto, Nishinomiya (JP); Tomomi Kuromiya, Matsusaka (JP); Daisuke Suzuki, Kofu (JP)

(73) Assignee: Chanel Parfums Beaute, Neuilly sur Seine (FR)

( * ) Notice: Subject to any disclaimer, the term of this patent is extended or adjusted under 35 U.S.C. 154(b) by 0 days.

(21) Appl. No.: 13/514,623

(22) PCT Filed: Dec. 3, 2010

(86) PCT No.: PCT/EP2010/068852
§ 371 (c)(1),
(2), (4) Date: Jun. 8, 2012

(87) PCT Pub. No.: WO2011/069915
PCT Pub. Date: Jun. 16, 2011

(65) Prior Publication Data
US 2012/0244204 A1    Sep. 27, 2012

(30) Foreign Application Priority Data

Dec. 11, 2009   (JP) .................................. 2009-281969

(51) Int. Cl.
*A61K 8/02* (2006.01)
*A61K 9/14* (2006.01)

(52) U.S. Cl.
USPC .......................................... 424/401; 424/489

(58) Field of Classification Search
USPC ........................ 424/489, 401, 402; 514/429
See application file for complete search history.

(56) References Cited

U.S. PATENT DOCUMENTS

| | | | |
|---|---|---|---|
| 6,066,312 A | | 5/2000 | Egawa et al. |
| 2009/0240070 A1 * | | 9/2009 | Kamachi et al. ............. 549/410 |

FOREIGN PATENT DOCUMENTS

| | | | |
|---|---|---|---|
| JP | 4-46144 A | | 2/1992 |
| JP | 7-228528 A | | 8/1995 |
| JP | 9-77726 A | | 3/1997 |
| JP | 2002-234836 A | | 8/2002 |
| JP | 2003-252747 A | | 9/2003 |
| JP | 2003-306419 A | | 10/2003 |
| JP | 2004-107262 A | | 4/2004 |
| JP | 2006-306744 A | | 11/2006 |
| JP | 2010-100564 A | | 5/2010 |
| WO | 00/37071 A1 | | 6/2000 |
| WO | 2006/114338 A1 | | 11/2006 |
| WO | WO 2006114338 A1 * | | 11/2006 |
| WO | 2007/091694 A1 | | 8/2007 |
| WO | WO 2007019694 A1 * | | 8/2007 |
| WO | WO 2007091694 * | | 8/2007 |
| WO | 2008/050173 A1 | | 5/2008 |
| WO | WO 2008050173 A1 * | | 5/2008 |

OTHER PUBLICATIONS

International Search Report, dated May 30, 2011, from corresponding PCT application.

* cited by examiner

*Primary Examiner* — Blessing M Fubara
(74) *Attorney, Agent, or Firm* — Young & Thompson

(57) ABSTRACT

A method for producing a composition for external use containing a physiologically acceptable salt of a tranexamate as an active ingredient, which is dispersed in the composition in the state of fine particles, includes dissolving a physiologically acceptable salt of the tranexamate in a solvent to prepare a solution, to which a salting-out agent is added to precipitate the salt. Such salt is so dispersed in a composition for external use in the state of fine particles, that the tranexamate salt can be mixed without using a large amount of an oil component to obtain a composition for external use affording excellent feel of use and stability.

11 Claims, No Drawings

COMPOSITION FOR EXTERNAL USE AND METHOD FOR PRODUCING THE SAME

TECHNICAL FIELD

The present invention relates to a composition for external use containing a physiologically acceptable salt of a tranexamate as an active ingredient, and a method for producing the same. It also relates to fine particles of this salt, and to a cosmetic composition comprising same.

BACKGROUND ART

Skin-whitening activity of a tranexamate has been known, and the same has been used as a skin-whitening ingredient in compositions for external use, such as drugs, quasi-drugs, and cosmetics. For example, Japanese Patent Laid-Open No. 04-46144 (Patent Document 1) discloses an anti-pigmentation agent for external use using a tranexamate as an active ingredient. Japanese Patent Laid-Open No. 2003-306419 (Patent Document 2) exemplifies tranexamic acid and derivatives thereof as a skin-whitening ingredient to be usable with Coenzyme Q10. Japanese Patent Laid-Open No. 2004-107262 (Patent Document 3) exemplifies cetyl tranexamate as an oil-soluble skin-whitening ingredient to be usable with an L-ascorbic acid tetra-branched fatty acid ester derivative.

However, there has been a problem that a tranexamate is sparingly-soluble in water or oil, and stable mixture thereof in a composition over an extended time period is difficult, and improvement of the solubility and the stability of the formulation have remained unsolved for successful formulation.

Japanese Patent Laid-Open No. 2002-234836 (Patent Document 4) discloses an anti-stress external preparation for skin using a tranexamate as an active ingredient. The same discloses a method to dissolve a tranexamate using a large amount of an oil component such as an olive oil. However, by this method, the formulation form is limited to a cream or a milky lotion due to the use of a large amount of an oil component. Additionally, the obtained external preparation is sticky and oily and the sense of use is unfavorable.

Further, Japanese Patent Laid-Open No. 2006-306744 (Patent Document 5) discloses an external preparation for skin using a tranexamate or a salt thereof as well as a silicone oil. The same teaches that by the combination of a tranexamate or a salt thereof and a silicone oil the solubility of the tranexamate or a salt thereof in the composition can be enhanced, and the activity of the tranexamate can last over an extended time period. Although a silicone oil is known as an oil component giving less heavy sense of use, due to the necessity of the use of a large amount of the same to dissolve the tranexamate, the range of choice for the formulation forms of the external preparation for skin becomes narrow.

SUMMARY OF THE INVENTION

Under such circumstances, provision of a formulation containing a tranexamate, which is suppressed of sticky or oily feeling and gives fresh and comfortable sense of use, has been desired. Further, provision of a formulation containing a tranexamate allowing a broad range of choice for the formulation forms has been needed.

The present inventor has studied intensively for coping with the problems to succeed in stably retaining an active ingredient derived from a tranexamate in a composition by dispersing a salt of the tranexamate in the composition in the state of fine particles, instead of dissolving the tranexamate in the composition. Furthermore, the inventor has also discovered that the salt of the tranexamate can be dispersed more stably by combining the salt with a water-soluble polymer selected from nonionic polymers and cationic polymers in the composition, thereby completing the present invention.

Namely, the present invention provides a method for producing a composition for external use in which a salt of a tranexamate is dispersed stably and stabilized fine particles of a salt of a tranexamate obtained by the method, as described hereinbelow. Furthermore, the present invention provides a composition containing a salt of a tranexamate wherein the salt is dispersed in the state of fine particles and a cosmetic method for inhibiting hyperpigmentation of and/or whitening the skin, for reducing aging spots or pigmentation spots by topical application to the skin of this composition.

A first object of this invention is thus a method for producing a composition for external use, the method comprising the steps of:

a) dissolving a physiologically acceptable salt of a tranexamate in a solvent, b) adding at least one salting-out agent into the obtained solution to precipitate the salt as crystals in the state of fine particles having an average particle size of 0.01 µm to 100 µm, and c) dispersing the precipitated salt in a composition for external use.

A second object of this invention is a composition for external use obtained by the above method.

A third object of this invention is the cosmetic use of the above composition for external use, for inhibiting pigmentation of and/or whitening the skin or for reducing aging spots or pigmentation spots.

A fourth object of this invention is a cosmetic method for inhibiting pigmentation of and/or whitening the skin or for reducing aging spots or pigmentation spots, the method comprising the topical application, to the skin, of the above composition for external use.

This invention also pertains to fine particles of a physiologically acceptable salt of a tranexamate obtainable by a method comprising the steps of:

a) dissolving a physiologically acceptable salt of a tranexamate in a solvent; and b) adding at least one salting-out agent into the obtained solution to precipitate crystals of the salt in the state of fine particles having an average particle size of 0.01 µm to 100 µm, and to a cosmetic composition comprising said fine particles.

EMBODIMENTS OF THE INVENTION

The composition for external use of the present invention and a method for producing the same will be described in more detail below.

The composition for external use of the present invention contains a physiologically acceptable salt of a tranexamate (hereinafter referred to also as "a tranexamate salt") as an active ingredient, in which composition the salt is dispersed in the state of fine particles.

Since the composition for external use of the present invention is composed of a tranexamate salt dispersed in the composition in the state of fine particles, crystal growth of the active ingredient due to environmental changes hardly occurs, and the active ingredient can remain dispersed in the composition stably for an extended time period. According to a preferred aspect of the present invention, the composition for external use of the present invention can express skin-whitening activity for a prolonged period.

The expression of "a state of fine particles" means herein that the particles are so minute that they disperse and remain suspended in a composition to make a white turbid appearance. The average particle size of the particles is 0.01 μm to 100 μm, preferably 0.05 μm to 50.0 μm, and more preferably 0.10 μm to 10.0 μm. Hereinafter, the above-mentioned steps a) to c) are described specifically.

(1) Step a)

Firstly, the step a) is described.

In the step a), a physiologically acceptable salt of a tranexamate is dissolved in a solvent. At this time, it is preferable that the tranexamate salt is dissolved in a solvent under stirring. Furthermore, the temperature of the solvent is preferably from 50 to 120° C., more preferably from 70 to 100° C., and further preferably from 80 to 90° C. Without wishing to be bound by any theory, it has been observed that the tranexamate salt formed micelles in the solvent.

In the present invention, it is preferable that the tranexamate used in the physiologically acceptable salt of a tranexamate is represented by the following formula (1),

[Chemical Formula 2]

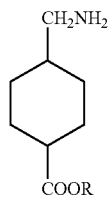

(1)

wherein R represents a group chosen from: a C1 to C22 linear saturated hydrocarbon group, a C2 to C22 linear unsaturated hydrocarbon group, or a $C_3$ to $C_{22}$ branched, saturated or unsaturated, hydrocarbon group, which may be substituted by at least one substituent selected from hydroxy and amino groups.

The hydrocarbon group may be aliphatic or aromatic or it may comprise both an aromatic and an aliphatic moieties. Examples of the hydrocarbon group include: an alkyl group, an alkenyl group, an alkynyl group, an alkyldienyl group, an aryl group, an alkylaryl group, an arylalkyl group, a cycloalkyl group, a cycloalkenyl group, and a cycloalkylalkyl group. Among them, an aliphatic hydrocarbon group, especially an alkyl group, is preferable. Its carbon number is preferably 8 to 20, and especially preferably 12 to 18.

There is no particular restriction of the number of substituents on the hydrocarbon group. In case the hydrocarbon group has 2 or more substituents, the substituents may be either hydroxy groups or amino groups, or both of hydroxy group(s) and amino group(s).

Specific examples of the tranexamate represented by Formula (I) include lauryl tranexamate, myristyl tranexamate, cetyl tranexamate and stearyl tranexamate. Among them, cetyl tranexamate is especially preferable.

Although there is no particular restriction on a physiologically acceptable salt of the tranexamate to be used in the present invention, insofar as the object of the present invention is not impeded, preferable examples thereof include a mineral acid salt, such as a hydrochloride salt, a phosphoric acid salt, a sulfuric acid salt, a bromic acid salt, and a nitric acid salt; an organic acid salt, such as an oxalic acid salt, a lactic acid salt, and a citric acid salt; and a carbonic acid salt of a tranexamate.

Among others a tranexamate salt to be used in the present invention should preferably be selected from the group consisting of a cetyl tranexamate hydrochloride salt, a cetyl tranexamate phosphoric acid salt, a cetyl tranexamate sulfuric acid salt, a cetyl tranexamate bromic acid salt, a cetyl tranexamate nitric acid salt, a cetyl tranexamate oxalic acid salt, a cetyl tranexamate lactic acid salt, a cetyl tranexamate citric acid salt, and a cetyl tranexamate carbonic acid salt. A cetyl tranexamate hydrochloride salt is especially preferable.

The tranexamate salt may be used singly or in combination of two or more types.

The tranexamate salt to be used as the source material can be obtained usually by an esterification method according to a dehydration condensation reaction between tranexamic acid having a carboxylic group and a higher alcohol having a hydroxy group. Tranexamic acid is a publicly known compound, which can be produced, for example, by a method disclosed in Japanese Patent Laid-Open No. 09-077726. The crystals of the tranexamate salt obtained by the above-mentioned method have usually the particle size of about 0.1 mm to 10.0 mm, and have a difficulty in being dissolved or dispersed directly and stably in a solvent. However, by dissolving the crystals of the tranexamate salt in a solvent and precipitating the salt by addition of a salting-out agent to the obtained solution in accordance with the method of the present invention, the tranexamate salt can be dispersed in the state of fine particles.

There is no particular restriction on the solvent to be used, examples thereof may include water; a lower alcohol (preferably, an alcohol having 1 to 5 carbon atoms), such as methanol, ethanol, propanol and isopropanol; a polyhydric alcohol, such as 1,3-butylene glycol, propylene glycol, dipropylene glycol and glycerin; an ether, such as ethyl ether and propyl ether; an ester, such as ethyl acetate and butyl acetate; a ketone, such as acetone and ethyl methyl ketone; and a mixture thereof. Among them, due to comparably high solubility, water or a mixture of water and a polar organic solvent is preferable, and especially water is preferable.

The concentration of a tranexamate salt after the tranexamate salt is dissolved in a solvent should be selected appropriately depending on the solubility of the tranexamate salt in the solvent to be used, and there is no particular restriction. For efficient precipitation of a tranexamate salt, the concentration is, for example, preferably 0.1 to 20.0% by weight, more preferably 0.5 to 10.0% by weight, and further preferably 1.0 to 5.0% by weight based on the total weight of the composition (solution obtained by dissolving a tranexamate salt and optionally other water-soluble components in a solvent).

(2) Step b)

Next, the step b) is described.

In the step b), the salt is precipitated by adding at least one salting-out agent to the solution obtained in the step a).

There is no particular restriction on the salting-out agent, insofar as a salt of a tranexamate in a solution can be precipitated. The sole requirement is thus that the salting-out agent be more soluble than the tranexamate salt in the solvent. Examples thereof include a citrate, an edetate, a glycolate, a phosphate, a hydrochloride, a sulfate, an acetate, a tartrate, a bromate, an oxalate, a lactate, a carbonate and a chloride salt. Among these salting-out agents a citrate, an edetate, a glycolate, a sulfate, a phosphate and a chloride salt are preferable, because a desired salt can be efficiently precipitated with a small amount of the salting-out agent and the compatibility with other components are good.

More specific examples include sodium citrate as a citrate; sodium edetate as an edetate; sodium glycolate as a glycolate; ammonium sulfate, sodium sulfate and magnesium sulfate as a sulfate; potassium phosphate and sodium phosphate as a phosphate; and sodium chloride and magnesium chloride as a chloride salt. Among these salting-out agents are more preferable sodium citrate, sodium edetate, sodium glycolate, sodium chloride, magnesium chloride and magnesium sulfate. The salting-out agent may be used singly or in combination of two or more types.

There is no particular restriction on salting-out conditions. The temperature when the salting-out agent is added to the solution obtained in the step a) is, for example, preferably 30 to 120° C., more preferably 40 to 100° C., and further preferably 60 to 90° C.

Further, in order to yield a salt in a uniform state of fine particles, the salting-out agent should preferably be added under stirring the solution.

Although there is no particular restriction on the amount of the salting-out agent to be used, it is preferably 0.05 to 5.0% by weight, more preferably 0.1 to 2.0% by weight, and further preferably 0.2 to 1.0% by weight based on the total weight of the composition (the mixture of the tranexamate salt, the solvent and the salting-out agent).

After the salting-out agent is added, a salt is precipitated preferably while stirring the obtained mixed solution. When the temperature of the mixed solution is higher than room temperature, the temperature of the mixed solution is preferably cooled to room temperature (20 to 40° C.). There is no particular restriction on the cooling rate. The solution may be cooled by using a temperature adjusting device or naturally cooled.

(3) Step c)

In the step c), the salt precipitated in the step b) is dispersed in a composition for external use in the state of fine particles having an average particle size of 0.01 μm to 100 μm. Note here that "an average particle size" used in the present application refers to a value (median size) measured (calculated) by using a laser diffraction particle size analyzer (SALD-7000, SHIMADZU).

In the present invention, the tranexamate salt may be isolated and collected from the composition obtained in step (c) and added to another composition for external use. There is no particular restriction on a method for isolating a tranexamate salt. Examples thereof include centrifugation, filtration, spray-drying and freeze-drying.

As mentioned above, this invention also pertains to a composition for external use that can be obtained in accordance with the above-mentioned steps a) to c).

There is no particular restriction on the content of the tranexamate salt dispersed in the composition for external use of the present invention, insofar as it gives an effective dose, and the content may be selected appropriately depending on the form of a formulation or a product. For example it is preferably 0.01 to 20.0% by weight, more preferably 0.1 to 10.0% by weight, and further preferably 0.5 to 5.0% by weight based on the total weight of the composition.

The composition for external use according to the present invention should preferably further contain a water-soluble polymer selected from nonionic polymers and cationic polymers. With the presence of a water-soluble polymer selected from nonionic polymers and cationic polymers in the composition, aggregation of a tranexamate salt can be suppressed even after a long period of storage, maintaining the stable dispersion state. The water-soluble polymer may be added after the precipitation of a tranexamate salt, or during the precipitation of the tranexamate salt. For example, a water-soluble polymer may be added in the step a) or b), or in the step c).

Examples of the water-soluble polymer selected from nonionic polymers and cationic polymers to be used in the present invention include polysaccharides, which may be modified, such as dextrin, cellulose derivatives including methyl cellulose, ethyl cellulose, sodium carboxymethyl cellulose, hydroxyethyl cellulose, hydroxypropyl cellulose or hydroxypropyl methyl cellulose stearoyl ester; glucomannan, xylan, mannan, and agar; synthetic polymers such as PVA (polyvinyl alcohol), PVM (polyvinyl methyl ether) or PVP (polyvinyl pyrrolidone); and natural gums such as locust bean gum, guar gum, tara gum or tamarind gum.

Among them, at least one selected from the group consisting of locust bean gum, guar gum, tara gum, hydroxyethyl cellulose, and hydroxypropyl methyl cellulose stearoyl ester is preferable.

The water-soluble polymer selected from nonionic polymers and cationic polymers may be used singly or in combination of two or more types.

There is no particular restriction on the content of the water-soluble polymer in the composition for external use of the present invention, insofar as it is in a range where the tranexamate salt can be maintained at a stable condition. For example, it is preferably 0.01 to 5.00% by weight, more preferably 0.05 to 2.00% by weight, and further preferably 0.1 to 1.00% by weight based on total weight of the composition for external use.

The pH of the composition for external use of the present invention generally ranges from 3.0 to 8.0 and preferably from 4.0 to 6.0 in view of adequate activity and improvement of safety.

According to the present invention an active ingredient derived from a tranexamate, which is instable between a dissolved and non-dissolved states, can be contained in the composition for external use in a stable condition for an extended time period by being dispersed in a composition in the state of fine particles. Since the tranexamate salt in the state of fine particles can be dispersed also in an aqueous medium, and it is not necessary to use a large amount of an oil component to disperse the active ingredient, a composition for external use with a refreshing sense of use suppressing sticky or oily feeling can be obtained. Furthermore, in case an oil component is added to the composition for external use, the content thereof can be appropriately adjusted according to the purpose, so that the range of selection for the form of a formulation or a product of the composition for external use can be broadened.

To the thus obtained composition for external use of the present invention, components to be used commonly in cosmetics or drugs, such as a powder component, a liquid oil, a solid fat, a wax, a hydrocarbon oil, a higher fatty acid, a higher alcohol (preferably an alcohol having 6 or more carbon atoms, and more preferably an alcohol having 10 or more carbon atoms), a synthetic ester oil, a silicone compound, a surfactant, a co-surfactant, a film forming agent, a gelling agent, a metal sequestering agent, a lower alcohol, a polyhydric alcohol or a derivative thereof, a monosaccharide, an oligosaccharide, an amino acid, a plant extract, an organic amine, a polymer emulsion, a cooling agent, a pH adjustor, a buffer, a perfume and water, may be appropriately added if needed to produce a desired formulation form according to a conventional method.

There is no particular restriction on the content of these additives, insofar as the object of the present invention is not impaired, and the content may be appropriately selected depending on the form of the formulation or the product. These additives may be added in any steps. The timing of adding these additives may be appropriately selected depending upon the kinds of additives.

Examples of a powder component include inorganic powders, such as talc, kaolin, mica, sericite, white mica, gold mica, a synthetic mica, red mica, black mica, vermiculite, magnesium carbonate, calcium carbonate, aluminum silicate, barium silicate, calcium silicate, magnesium silicate, strontium silicate, a metal tungstate, silica, zeolite, barium sulfate, calcined calcium sulfate (calcined gypsum), calcium phosphate, fluorine apatite, hydroxyapatite, ceramic powder, metallic soap (e.g. zinc myristate, calcium palmitate and aluminum stearate) and boron nitride; organic powders, such as polyamide resin powder (nylon powder), polyethylene powder, polymethyl methacrylate powder, polystyrene powder, styrene/acrylic acid copolymer resin powder, benzoguanamine resin powder, polytetrafluoroethylene powder and cellulose powder; metal powder pigments, such as aluminum powder and copper powder; organic pigments, such as a zirconium-, barium-, and aluminum-lakes; and natural colors, such as chlorophyll and β-carotene.

Examples of a liquid oil include avocado oil, camellia oil, turtle oil, *macadamia* nut oil, corn oil, mink oil, olive oil, rapeseed oil, yolk oil, sesame oil, persic oil, wheat germ oil, camellia kissi oil, castor oil, linseed oil, safflower oil, cotton seed oil, *perilla* oil, soybean oil, peanut oil, tea seed oil, Torreya seed oil, rice bran oil, Chinese tung oil, Japanese tung oil, jojoba oil, germ oil, and triglycerin.

Examples of a solid fat include cacao butter, coconut oil, horse tallow, hardened coconut oil, palm oil, beef tallow, mutton tallow, hardened beef tallow, palm kernel oil, lard, cattle bone fat, Japan tallow kernel oil, hardened oil, neatsfoot oil, Japan tallow, and hardened castor oil.

Examples of a wax include bees wax, candelilla wax, cotton wax, carnauba wax, bayberry wax, Chinese insect wax, spermaceti, montan wax, bran wax, lanolin, kapok wax, acetylated lanolin, liquid lanolin, sugar cane wax, lanolin fatty acid isopropyl ester, hexyl laurate, reduction lanolin, jojoba wax, hard lanolin, shellac wax, POE lanolin alcohol ether, POE lanolin alcohol acetate, POE cholesterol ether, lanolin fatty acid polyethylene glycol, and POE hydrogenated lanolin alcohol ether.

Examples of a hydrocarbon oil include liquid paraffin, ozokerite, squalane, pristane, paraffin, ceresin, squalene, vaseline, microcrystalline wax, and hydrogenated polydecene.

Examples of a higher fatty acid include lauric acid, myristic acid, palmitic acid, stearic acid, behenic acid, oleic acid, undecylenic acid, tall oil acid, isostearic acid, linoleic acid, linolenic acid, eicosapentaenoic acid (EPA), and docosahexaenoic acid (DHA).

Examples of a higher alcohol include linear alcohols, such as lauryl alcohol, cetyl alcohol, stearyl alcohol, behenyl alcohol, myristyl alcohol, oleyl alcohol, and cetostearyl alcohol; branched alcohols, such as monostearyl glyceryl ether (batyl alcohol), 2-decyltetradecanol, lanolin alcohol, cholesterol, phytosterol, hexyldodecanol, isostearyl alcohol, and octyldodecanol.

Examples of a synthetic ester oil include tripropylene glycol dineopentanoate, isononyl isononanoate, isopropyl myristate, cetyl octanoate, octyldodecyl myristate, isopropyl palmitate, butyl stearate, hexyl laurate, myristyl myristate, decyl oleate, hexyldecyl dimethyloctanoate, cetyl lactate, myristyl lactate, acetylated lanolin, isocetyl stearate, isocetyl isostearate, cholesteryl 12-hydroxystearate, ethylene glycol di-2-ethylhexanoate, dipentaerythritol fatty acid ester, N-alkylglycol monoisostearate, neopentyl glycol dicaprylate, diisostearyl malate, glyceryl di-2-heptylundecanoate, trimethylolpropane tri-2-ethylhexanoate, trimethylolpropane triisostearate, pentaerythritol tetra-2-ethylhexanoate, glyceryl tri-2-ethylhexanoate, glyceryl trioctanoate, glyceryl triisopalmitate, trimethylolpropane triisostearate, cetyl 2-ethylhexanoate, 2-ethylhexyl palmitate, glyceryl trimyristate, glyceride tri-2-heptylundecanoate, castor oil fatty acid methyl ester, oleyl oleate, acetoglyceride, 2-heptylundecyl palmitate, diisobutyl adipate, N-lauroyl-L-glutamic acid-2-octyldodecyl ester, di-2-heptylundecyl adipate, ethyl laurate, di-2-ethylhexyl sebacate, 2-hexyldecyl myristate, 2-hexyldecyl palmitate, 2-hexyldecyl adipate, diisopropyl sebacate, 2-ethylhexyl succinate, and triethyl citrate.

Examples of a silicone compound include silicone oils, including linear polysiloxanes such as dimethylpolysiloxane, methylphenylpolysiloxane and diphenylpolysiloxane and cyclic polysiloxanes, such as octamethyl cyclotetrasiloxane, decamethyl cyclopentasiloxane and dodecamethyl cyclohexasiloxane; silicone resins forming a 3D net structure; silicone elastomers; various modified polysiloxanes, such as aminomodified polysiloxane, polyether-modified polysiloxane, alkyl-modified polysiloxane and fluorine-modified polysiloxane.

Examples of silicone elastomers include non-emulsifying organopolysiloxane elastomers or emulsifying organosiloxane elastomers. Examples of the non-emulsifying organopolysiloxane elastomers include dimethicone/vinyl dimethicone crosspolymers, lauryl dimethicone/vinyl dimethicone crosspolymers, and the like.

The dimethicone/vinyl dimethicone crosspolymers include products commercially available from DOW CORNING under the trade name of, for example, DC 9040 and DC 9045; products commercially available from GENERAL ELECTRIC under the trade name of SFE 839 and the Velvasil series products; products commercially available from SHIN ETSU under the trade name of, for example, KSG-15, KSG-16, and KSG-18 ([dimethicone/phenyl vinyl dimethicone crosspolymer]); and Gransil™ series products from GRANT INDUSTRIES.

The lauryl dimethicone/vinyl dimethicone crosspolymers include products commercially available from SHIN ETSU under the trade name of, for example, KSG-31, KSG-32, KSG-41, KSG-42, KSG-43, and KSG-44.

Examples of the emulsifying organosiloxane elastomers include polyalkoxylated silicone elastomers, polyglycerolated silicone elastomers, or the like.

The polyalkoxylated silicone elastomers include products commercially available from DOW CORNING under the trade name of, for example, DC9010 and DC9011; products commercially available from SHIN ETSU under the trade name of, for example, KSG-20, KSG-21, KSG-30, KSG-31, KSG-32, KSG-33, KSG-210, KSG-310, KSG-320, KSG-330, KSG-340, and X-226146.

The polyglycerolated silicone elastomers include products commercially available from SHIN ETSU under the trade name of, for example, KSG-710, KSG-810, KSG-820, KSG-830, KSG-840, KSG-31, KSG-32, KSG-41, KSG-42, KSG-43, and KSG-44.

Further, a silicone resin-hydrolyzed protein can be also used. Examples of a silicone resin-hydrolyzed protein include (hydrolyzed silk/PG-propyl methylsilanediol)crosspolymer and (trimethylsilyl hydrolyzed wheat protein/PG-propyl methylsilanediol)crosspolymer. A commercially available product may be used as a silicone resin-hydrolyzed protein. Examples of such a commercially available product include products of Seiwa Kasei Co., Ltd. under the trade names of PROTESIL FN, PROTESIL LH, and PROTESIL GLH.

Examples of a surfactant include a lipophilic nonionic surfactant and a hydrophilic nonionic surfactant.

Examples of a lipophilic nonionic surfactant include a sorbitan fatty acid ester, such as sorbitan monooleate, sorbitan monoisostearate, sorbitan monolaurate, sorbitan monopalmitate, sorbitan monostearate, sorbitan sesquioleate, sorbitan trioleate, diglycerol sorbitan penta-2-ethylhexylate and diglycerol sorbitan tetra-2-ethylhexylate; a glyceryl polyglyceryl fatty acid, such as glyceryl mono-cotton seed oil fatty acid, glyceryl monoerucate, glyceryl sesquioleate, glyceryl monostearate, glyceryl α,α'-oleate pyroglutamate, and glyceryl monostearate malate; a propylene glycol fatty acid ester such as monostearate propylene glycol; a hydrogenated castor oil derivative; and a glycerin alkyl ether.

Examples of a nonionic surfactant oil include a POE-sorbitan fatty acid ester, such as POE-sorbitan monooleate, POE-sorbitan monostearate, POE-sorbitan monooleate and POE-sorbitan tetraoleate; a POE sorbitol fatty acid ester, such as POE-sorbitol monolaurate, POE-sorbitol monooleate, POE-sorbitol pentaoleate, POE-sorbitol monostearate; a POE-glycerin fatty acid ester, such as POE-glycerin monooleate, POE-glycerin monostearate, POE-glycerin monoisostearate and POE-glycerin triisostearate; a POE-fatty acid ester, such as POE-monooleate, POE-distearate, POE-monodioleate and ethylene glycol distearate; a POE-alkyl ether, such as POE-lauryl ether, POE-oleyl ether, POE-stearyl ether, POE-behenyl ether, POE-2-octyldodecyl ether and POE-cholestanol ether; a Pluronic type surfactant (e.g. Pluronic); a POE-POP-alkyl ether, such as POE-POP-cetyl ether, POE-POP-2-decyltetradecyl ether, POE-POP-monobutyl ether, POE-POP-hydrogenated lanolin and POE-POP-glycerin ether.

Examples of co-surfactants include higher alcohols. Among them, linear fatty alcohols such as lauryl alcohol, cetyl alcohol, stearyl alcohol, behenyl alcohol, myristyl alcohol, oleyl alcohol, cetostearyl alcohol, and the like, are preferable. Cetyl alcohol is further preferable.

Examples of a gelling agents include nonionic polymers, cationic polymers, as well as anionic polymers and amphoteric polymers with an anionic group, such as gum Arabic, carrageenan, karaya gum, Tragacanth gum, *Pyrus cydonia* seed (marmelo), casein, gelatin, sodium pectate, sodium alginate, xanthan gum, pectin, fucoidan, galactomannan, curdlan, gellan gum, Fucogel® (a fucose-rich polysaccharide), collagen, sodium hyaluronate, Alcasealan® (a polysaccharide produced by *alcaligenes*), propylene glycol alginate, and dialkyl dimethyl ammonium cellulose sulfate).

Examples of a metal sequestering agent include 1-hydroxyethane-1,1-diphosphonic acid; 1-hydroxyethane-1,1-diphosphonic acid tetrasodium salt; disodium edetate; trisodium edetate; tetrasodium edetate; sodium citrate; sodium polyphosphate; sodium metaphosphate; gluconic acid; phosphoric acid; citric acid; ascorbic acid; succinic acid; edetic acid; and trisodium ethylenediamine hydroxyethyl triacetate.

Examples of a lower alcohol include ethanol, propanol, isopropanol, isobutyl alcohol, and t-butyl alcohol.

Examples of a polyhydric alcohol or a derivative thereof include a dihydric alcohol, such as ethylene glycol, propylene glycol, pentylene glycol, trimethylene glycol, 1,2-butylene glycol, 1,3-butylene glycol, tetramethylene glycol, 2,3-butyleneglycol, pentamethylene glycol, 2-butene-1,4-diol, hexylene glycol and octylene glycol; a trihydric alcohol, such as glycerin and trimethylolpropane; a tetrahydric alcohol such as pentaerythritol (e.g. 1,2,6-hexanetriol); a pentahydric alcohol such as xylitol; a hexahydric alcohol, such as sorbitol and mannitol; a polyhydric alcohol polymer, such as diethylene glycol, dipropylene glycol, triethylene glycol, polypropylene glycol and tetraethylene glycol; a dihydric alcohol alkyl ether, such as ethylene glycol monomethyl ether and ethylene glycol monoethyl ether; a dihydric alcohol alkyl ether, such as diethylene glycol monomethyl ether, diethylene glycol monoethyl ether and diethylene glycol monobutyl ether; a dihydric alcohol ether ester, such as ethylene glycol monomethyl ether acetate and ethylene glycol monoethyl ether acetate; a glyceryl monoalkyl ether, such as chimyl alcohol, selachyl alcohol and batyl alcohol; and a sugar alcohol, such as sorbitol, maltitol, maltotriose, mannitol, sucrose, erythritol, glucose, fructose, starch sugar, maltose, xylitose, and a reduced alcohol of a starch sugar.

Examples of a monosaccharide include a triose, such as D-glyceryl aldehyde and dihydroxyacetone; a tetrose, such as D-erythrose, D-erythrulose, D-threose and erythritol; a pentose, such as L-arabinose, D-xylose, L-lyxose, D-arabinose, D-ribose, D-ribulose, D-xylulose and L-xylulose; a hexose, such as D-glucose, D-talose, D-psicose, D-galactose, D-fructose, L-galactose, L-mannose and D-tagatose; a heptose, such as aldoheptose and heprose; an octose such as octurose; a deoxy sugar, such as 2-deoxy-D-ribose, 6-deoxy-L-galactose and 6-deoxy-L-mannose; an amino sugar, such as D-glucosamine, D-galactosamine, sialic acid, amino uronic acid and muramic acid; a uronic acid, such as D-glucuronic acid, D-mannuronic acid, L-guluronic acid, D-galacturonic acid and L-iduronic acid.

Examples of an oligosaccharide include sucrose, lactose, maltose, trehalose, cellobiose, gentiobiose, umbilicin, raffinose, gentianose, maltotriose, melezitose, planteose, unbelliferose, stachyose, and verbascose.

Examples of an amino acid include a neutral amino acid, such as threonine and cysteine; and a basic amino acid such as hydroxylysine. Further, as an amino acid derivative, such as sodium acyl sarcosinate (sodium lauroyl sarcosinate), acyl glutamate, sodium acyl β-alanine, glutathione, and pyrrolidone carboxylic acid may be exemplified.

Examples of an organic amine include monoethanolamine, diethanolamine, triethanolamine, morpholine, triisopropanolamine, 2-amino-2-methyl-1,3-propanediol, and 2-amino-2-methyl-1-propanol.

Examples of a polymer emulsion include an acrylic resin emulsion, a poly(ethyl acrylate) emulsion, an acrylic resin solution, a poly(alkyl acrylate) emulsion, a poly(vinyl acetate) emulsion, and a natural rubber latex.

These additives are mentioned in International Cosmetic Ingredient Dictionary and Handbook, 9th Edition, 2002, published by the Cosmetic, Toiletry and Fragrance Association, which can be referred to.

The composition for external use according to the present invention may further contain various active agents such as vitamins, antioxidants, moisturizing agents, blood flow promoters, antibacterial agents, cell (skin) activating agents, emollients, anti-aging agents, anti-pollution agents, keratolytic agents, astringents, anti-inflammatory agents, whitening agents, and sunscreens.

Examples of a vitamin include vitamins A, $B_1$, $B_2$, $B_6$, C and E and derivatives thereof, pantothenic acid and derivatives thereof and biotin.

Examples of antioxidants include ascorbic acid and its derivatives such as ascorbyl palmitate, ascorbyl tetraisopalmitate, ascorbyl glucoside, magnesium ascorbyl phosphate, sodium ascorbyl phosphate and ascorbyl sorbate; tocopherol and its derivatives, such as tocopheryl acetate, tocopheryl sorbate, and other esters of tocopherol; dibutyl hydroxytoluene (BHT) and butylated hydroxyanisole (BHA); gallic acid ester; phosphoric acid; citric acid; maleic acid; malonic acid; succinic acid; fumaric acid; cephalin; a hexametaphosphate; phytic acid; ethylenediaminetetraacetic acid; and plant extracts, for instance from *Chondrus cripsus, Rhodiola, Thermus thermophilus*, mate leaf, oak wood, kayu rapet bark, sakura leaves and ylang ylang leaves.

Examples of moisturizing agent include polyethylene glycol; propylene glycol; dipropylene glycol; glycerin; 1,3-butylene glycol; xylitol; sorbitol; maltitol; mucopolysaccharides, such as chondroitin sulfuric acid; hyaluronic acid; sodium hyaluronate, sodium acetylated hyaluronate, mucoitinsulfuric acid; caronic acid; atelo-collagen; cholesteryl-12-hydroxystearate; bile salt; a main component of NMF (natural moisturizing factor), such as a pyrrolidone carboxylic acid salt, and a lactic acid salt; amino acids such as urea, cysteine and serine; short-chain soluble collagen; a diglycerin (EO) PO addition product; homo- and copolymers of 2-methacryloyloxyethylphosphorylcholine commercially available from NOF under the name of, for example, Lipidure HM and Lipidure PBM; panthenol; allantoin; PEG/PPG/Polybutylene Glycol-8/5/3 Glycerin commercially available from NOF under the trade name of Wilbride S 753; Trimethylglycine commercially available from Asahi KASEI Chemicals under the trade name of AMINOCOAT; and various plant extracts such as *Castanea sativa* extracts, hydrolyzed hazelnut proteins, *Polianthes tuberosa* polysaccharides, *Argania spinosa* kernel oil, and an extract of pearl containing conchiolin commercially available from Maruzen Pharmaceuticals under the trade name of Pearl Extract™.

Examples of emollients include glyceryl polymethacrylate, methyl gluceth-20, and the like.

Examples of anti-aging agents include acyl amino acids (specifically, products commercially available from SEDERMA under the trade name of Maxilip, Matrixyl 3000 or Biopeptide CL, or product commercially available from SEPPIC under the trade name of Sepilift); *Pisum sativum* extracts; hydrolyzed soy proteins; methylsilanol mannuronate; hydrolyzed *cucurbita* pepo seedcake; Scenedesmus extract; and the like.

Examples of anti-pollution agents include Moring a pterygosperma seed extracts (specifically, product commercially available from LSN under the trade name of Purisoft); Shea butter extract (specifically, products commercially available from SILAB under the trade name of Detoxyl, a blend of ivy extract, phytic acid, sunflower seed extract (for example, product commercially available from SEDERMA under the trade name of OSMOPUR), and the like.

Examples of keratolytic agents include α-hydroxy acids (specifically, glycolic, lactic, citric, malic, mandelic or tartaric acid) and β-hydroxy acids (specifically, salicylic acid), and their esters (specifically, $C_{12-13}$ alkyl lactate), plant extracts containing these hydroxy acids (specifically, Hibiscus sabdriffa extracts), and the like.

Examples of astringents include hamamelis extracts, and the like.

Examples of anti-inflammatory agents include bisabolol, allantoin, tranexamic acid, zinc oxide, sulfur oxide and its derivatives, chondroitin sulfate, glycyrrhizinic acid and its derivatives (for example, glycyrrhizinates).

The composition for external use according to the present invention may contain at least one whitening agent to block the synthesis of structural proteins such as the melanocyte-specific glycoprotein Pmel17 involved in the mechanism of melanogenesis (stage I). Example of such a whitening agent may include the ferulic acid-containing cytovector (water, glycol, lecithin, ferulic acid, hydroxyethylcellulose) commercially available from BASF under the trade name Cytovector™.

Furthermore, if necessary, the composition for external use according to the present invention may contain at least one peptide as described in the patent application WO2009/010356.

Furthermore, if necessary, the composition for external use according to the present invention may include a whitening agent having an inhibition effect on melanin synthesis and/or an inhibition effect on nanophthalmia-related transcription factor (MITE) expression and/or an anti-tyrosinase activity and/or an inhibition effect on endothelin-1 synthesis. Examples of such a whitening agent may include *Glycyrrhiza glabra* extract commercially available from Maruzen Pharmaceuticals under the trade name Licorice Extract™.

Furthermore, if necessary, the composition for external use according to the present invention may include whitening agents having an antioxidant effect as well, such as vitamin C compounds, which include ascorbate salts, ascorbyl esters of fatty acids or of sorbic acid, and other ascorbic acid derivatives. Specific examples include ascorbyl phosphates (magnesium ascorbyl phosphate, sodium ascorbyl phosphate, and the like), saccharide esters of ascorbic acid (ascorbyl-2-glucoside, 2-O-α-D-glucopyranosyl L-ascorbate, or 6-O-β-D-galactopyranosyl L-ascorbate, and the like). Active agents of this type are commercially available from DKSH under the trade name of Ascorbyl Glucoside™.

Furthermore, if necessary, the composition for external use according to the present invention may include other whitening agents. Example of the other whitening agents include pigmentation inhibiting agents such as plant extracts (Narcissus tazetta extracts), arbutin, kojic acid, ellagic acid, cysteine, 4-thioresorcin, resorcinol or rucinol or their derivatives, glycyrrhizinic acid, hydroquinone-β-glucoside, and the like.

Furthermore, if necessary, the composition for external use according to the present invention may also include organic and/or inorganic sunscreens.

Examples of the organic sunscreens may include dibenzoylmethane derivatives such as butyl methoxydibenzoylmethane (product commercially available from HOFFMANN LA ROCHE under the trade name of Parsol 1789); cinnamic acid derivatives such as ethylhexyl methoxycinnamate (product commercially available from HOFFMANN LA ROCHE under the trade name of Parsol MCX), salicylates, para-aminobenzoic acids; β-β'-diphenylacrylate derivatives; benzophenone derivatives; benzylidenecamphor derivatives such as terephtalylidene dicamphor sulphonic acid; phenylbenzimidazole derivatives; triazine derivatives; phenylbenzotriazole derivatives; anthranilic derivatives, and the like, all of which may be coated or encapsulated.

Examples of the inorganic sunscreens may include nanopigments formed from coated or uncoated metal oxides, such as, for example, titanium oxide, iron oxide, zinc oxide, zirconium oxide or cerium oxide nanopigments; which are all UV photoprotective agents well known per se.

The formulation form of the composition for external use of the present invention is arbitrarily selectable, and any of a solution type, an emulsion type, a and a gel type can be adapted. Moreover, as indicated above, the tranexamate crystals may be isolated from this composition and introduced in another composition for external use, which can be a liquid or semi-liquid or solid composition of any type, including solutions, emulsions, gels, but also powders optionally including a water and/or oil phase therein.

Further, the product form of these compositions for external use is also arbitrarily selectable, and the composition is applicable to facial cosmetics, such as a facial cleanser, a face lotion, an essence liquid, a milky lotion, a cream and a pack; makeup cosmetics, such as a foundation, a lipstick and an eye shadow; body makeup products; hair care cosmetics; oral care toiletries; perfumeries; cleansers; and ointments.

EXAMPLES

The present invention will now be described in more detail by way of examples and comparative examples, provided that the present invention be not limited thereto.

Examples 1 to 6

The compositions for external use according to the compositions of Table 1 were prepared as follows.

The components 1 to 3 were dissolved under heated and stirring at 85±5° C., and the composition was kept at 85±5° C. with stirring, to which the components B heated to 70±5° C. were added gradually. The resulting composition was cooled down to room temperature (25±5° C.) under stirring, which pH was then adjusted to 5.0±0.5 by the component 5 or 6.

TABLE 1

|  |  | Unit: % by weight Examples | | | | | |
|---|---|---|---|---|---|---|---|
| Components | | 1 | 2 | 3 | 4 | 5 | 6 |
| 1. Purified water | | Balance | Balance | Balance | Balance | Balance | Balance |
| 2. Component A: cetyl tranexamate hydrochloride salt*[1] | | 1.0 | 2.0 | 2.0 | 3.0 | 3.0 | 6.0 |
| 3. Polyoxyethylene cetyl ether (40EO) | | 0.2 | 0.2 | 0.2 | 0.2 | 0.2 | 0.2 |
| 4. Components B | 10% by weight aq. solution of sodium citrate | 6.0 | 6.0 | 6.0 | 8.0 | 10.0 | 12.0 |
|  | 10% by weight aq. solution of sodium edetate | — | — | 1.0 | — | — | — |
|  | 10% by weight aq. solution of sodium glycolate | — | — | — | — | 2.0 | 2.0 |
| 5. 10% by weight aq. solution of hydrochloric acid | | q.s. | q.s. | q.s. | q.s. | q.s. | q.s. |
| 6. 10% by weight aq. solution of sodium hydroxide | | q.s. | q.s. | q.s. | q.s. | q.s. | q.s. |
| Total | | 100 | 100 | 100 | 100 | 100 | 100 |

*[1] "NIKKOL TXC" (trade name) of Nikko Chemicals Co. Ltd. was used.
Appearance: white-yellowish crystalline powder
Melting point: 131 to 135° C., Weight loss on drying: 1.0% or less (105° C., 2 hours)

Comparative Examples 1 to 3

Except that the compositions according to Table 2 were used, compositions for external use were prepared identically to Examples 1 to 6.

TABLE 2

|  |  | Unit: % by weight Comparative Examples | | |
|---|---|---|---|---|
| Components | | 1 | 2 | 3 |
| 1. Purified water | | Balance | Balance | Balance |
| 2. Component A: cetyl tranexamate hydrochloride salt *[1] | | 1.0 | 2.0 | 6.0 |
| 3. Polyoxyethylene cetyl ether (40EO) | | 0.2 | 0.2 | 0.2 |
| 4. Components B | 10% by weight aq. solution of sodium citrate | — | — | — |
|  | 10% by weight aq. solution of sodium edetate | — | — | — |
|  | 10% by weight aq. solution of sodium glycolate | — | — | — |
| 5. 10% by weight aq. solution of hydrochloric acid | | q.s. | q.s. | q.s. |
| 6. 10% by weight aq. solution of sodium hydroxide | | q.s. | q.s. | q.s. |
| Total | | 100 | 100 | 100 |

*[1] "NIKKOL TXC" (trade name) of Nikko Chemicals Co. Ltd. was used.
Appearance: white - yellowish crystalline powder
Melting point: 131 to 135° C.,
Weight loss on drying: 1.0% or less (105° C., 2 hours)

[Evaluation of Stability on Examples 1 to 6 and Comparative Examples 1 to 3]

The skin care formulations for external use according to Examples 1 to 6 and Comparative Examples 1 to 3 were left standing overnight at room temperature (20 to 25° C.), and presence of aggregates and the crystal precipitation state were observed visually. The results are shown in Table 3.

TABLE 3

|  | Stability |
|---|---|
| Example 1 | White turbid dispersion |
| Example 2 | White turbid dispersion |
| Example 3 | White turbid dispersion |
| Example 4 | White turbid dispersion |
| Example 5 | White turbid dispersion |
| Example 6 | White turbid dispersion |
| Comparative Example 1 | With precipitated crystals |
| Comparative Example 2 | With precipitated crystals |
| Comparative Example 3 | With precipitated crystals |

As shown in Table 3, cetyl tranexamate hydrochloride salts in the compositions for external use according to Examples 1 to 6 were obtained in the state of a uniform fine particle suspension with white turbid appearance. On the other hand, according to Comparative Examples 1 to 3, crystals of cetyl tranexamate hydrochloride salts were present as precipitated aggregates.

[Evaluation of Particle Size Distribution in Examples 1 to 6 and Comparative Examples 1 to 3]

In the skin care formulations for external use according to Examples 1 to 6 and Comparative Examples 1 to 3, the particle size distribution of fine particles of cetyl tranexamate hydrochloride salt in Examples 1 to 6 in which a dispersing state of fine particles were obtained after standing overnight at room temperature (20 to 25° C.) were measured by using a laser diffraction particle size analyzer (SALD-7000, SHIMADZU).

Samples were put into a flow cell, which had been filled with circulating distilled water in advance, until an appropriate concentration was obtained, and then measured. The results are shown in Table 4 in median size.

TABLE 4

|  | Example 1 | Example 2 | Example 3 | Example 4 | Example 5 | Example 6 |
| --- | --- | --- | --- | --- | --- | --- |
| Particle size distribution: median size (μm) | 2.8 | 4.3 | 10.7 | 7.9 | 8.6 | 17.8 |

As shown in Table 4, it was confirmed that the fine particles of the cetyl tranexamate hydrochloride salt dispersed in the compositions for external use in Examples 1 to 6 had constant particle sizes.

Examples 7 to 16

The compositions for external use having the compositions shown in Table 5 were prepared as follows.

The water phase components 1 to 6 and the oil phase components 7 to 14 were dissolved under stirring with heating at 85±5° C. respectively. To the water phase components whose temperature was kept at 85±5° C., the oil phase components were added with stirring, and then the component B warmed to 70±5° C. was added, which was then cooled down to room temperature (25±5° C.) under stirring.

TABLE 5

|  | Components | Unit: % by weight Contents |
| --- | --- | --- |
| Water phase | 1. Purified water | Balance |
|  | 2. Component A: cetyl tranexamate hydrochloride salt *1 | 1.0 |
|  | 3. Pentyleneglycol | 2.5 |
|  | 4. Polyoxyethylene methyl glucoside (10EO) | 2.5 |
|  | 5. Methylparaben | 0.2 |
|  | 6. Water-soluble polymer | q.s. *2 |
| Oil phase | 7. Cetyl alcohol | 3.0 |
|  | 8. Glyceryl monostearate | 0.2 |
|  | 9. Sorbitan monostearate | 0.2 |
|  | 10. Polyoxyethylene sorbitan monostearate (20EO) | 0.2 |
|  | 11. Polyoxyethylene sorbitol tetraoleate (40EO) | 0.5 |
|  | 12. Cetyl 2-ethylhexanoate | 2.0 |
|  | 13. Dimethylpolysiloxane | 3.0 |
|  | 14. Propylparaben | 0.1 |

TABLE 5-continued

|  | Components | Unit: % by weight Contents |
| --- | --- | --- |
| 15. Component B: 10% by weight aq. solution of sodium citrate |  | 2.0 |
| Total |  | 100 |

*1 "NIKKOL TXC" (trade name) of Nikko Chemicals Co. Ltd. was used.
Appearance: white - yellowish crystalline powder
Melting point: 131 to 135° C.,
Weight loss on drying: 1.0% or less (105° C., 2 hours)
*2 Water soluble polymer used is shown in Table 5.

[Evaluation of Stability on Examples 7 to 16]

The conditions of the prepared compositions for external use of Examples 7 to 16 were observed visually immediately after the preparation, after standing overnight after the preparation at room temperature (20 to 25° C.), and after standing for 2 weeks or 2 months after the preparation at 45° C. The conditions of the compositions for external use were evaluated according to the following rating scale. The results are shown in Table 6.

(Rating Scale)

⊚: A uniform composition for external use was obtained immediately after preparation, and the same condition was kept over storage for 2 months at 45° C.;

○: A uniform composition for external use was obtained immediately after preparation, and the same condition was kept over storage for 2 weeks at 45° C.;

Δ: A uniform composition for external use was obtained immediately after preparation, but separation or aggregation was observed after storage for 2 weeks at 45° C.; and x: Aggregates were observed immediately after preparation, and therefore a uniform composition for external use was not obtained.

TABLE 6

|  |  | Water-soluble polymer | Unit: % by weight Content | Rating |
| --- | --- | --- | --- | --- |
| Example | 7 | Locust bean gum | 0.5 | ⊚ |
|  | 8 | Guar gum | 0.5 | ⊚ |
|  | 9 | Tara gum | 0.5 | ⊚ |
|  | 10 | Mannan | 0.5 | ○ |
|  | 11 | Agar | 1.0 | ○ |
|  | 12 | Hydroxyethyl cellulose | 0.5 | ⊚ |
|  | 13 | Hydroxypropyl cellulose | 0.5 | ○ |
|  | 14 | Hydroxypropyl methyl cellulose | 0.5 | ○ |
|  | 15 | Hydroxypropyl methyl cellulose stearoyl ester | 0.5 | ⊚ |
|  | 16 | Cationized guar gum | 0.5 | Δ |

As shown in Table 5, the compositions for external use according to Examples 7 to 16 were obtained in the state of a uniform fine particle dispersion with white turbid appearance. Especially in case locust bean gum, guar gum, tara gum, hydroxyethyl cellulose, or hydroxypropyl methyl cellulose stearoyl ester was used as a water-soluble polymer, excellent stability was recognized even at a temperature as high as 45° C.

Examples 17 to 24

The compositions for external use (a W/O-type essence liquid) according to the compositions of Table 7 were prepared as follows.

The water phase components 1 to 9 and the oil phase components 10 to 19 were dissolved respectively under heating and stirring at 85±5° C., and the oil phase components were added with stirring to the water phase components kept at 80±5° C. To the mixture the components B and the powder components were added with stirring, which was then cooled down to room temperature (25±5° C.) under stirring. In Examples 17 and 24, component C was added during cooling with stirring.

TABLE 7

Unit: % by weight

|  | Components | Example 17 | 18 | 19 | 20 | 21 | 22 | 23 | 24 |
|---|---|---|---|---|---|---|---|---|---|
| Water phase | 1. Purified water | Balance | Balance | Balance | Balance | Balance | Balance | Balance | Balance |
|  | 2. Component A: cetyl tranexamate hydrochloride salt *1 | 1.0 | 2.0 | 3.0 | 3.0 | 3.0 | 3.0 | 5.0 | 5.0 |
|  | 3. Pentyleneglycol | 2.5 | 2.5 | 2.5 | 2.5 | 2.5 | 2.5 | 2.5 | 2.5 |
|  | 4. Polyoxyethylene methyl glucoside (10EO) | 2.0 | 2.0 | 2.0 | 2.0 | 2.5 | 2.5 | 2.5 | 2.5 |
|  | 5. Raffinose | — | — | — | 1.0 | 1.0 | — | — | — |
|  | 6. Chlorphenesin | — | — | 0.2 | 0.2 | — | — | — | — |
|  | 7. Methylparaben | 0.2 | 0.2 | 0.2 | 0.2 | 0.2 | 0.2 | 0.2 | 0.2 |
|  | 8. Guar gum | 0.2 | 0.1 | — | — | 0.1 | 0.2 | 0.2 | 0.2 |
|  | 9. Hydroxyethyl cellulose | — | 0.1 | 0.2 | 0.2 | 0.1 | — | 0.2 | 0.2 |
| Oil phase | 10. Cetyl alcohol | 3.0 | 3.0 | 3.0 | 3.0 | 3.0 | 3.0 | 3.0 | 3.0 |
|  | 11. Glyceryl monostearate | 0.2 | 0.2 | 0.2 | 0.1 | 0.2 | 0.2 | 0.2 | 0.2 |
|  | 12. Sorbitan monostearate | 0.2 | 0.2 | 0.2 | 0.2 | 0.2 | 0.2 | 0.2 | 0.2 |
|  | 13. Polyoxyethylene sorbitan monostearate (20EO) | 0.2 | 0.2 | 0.2 | 0.3 | 0.2 | 0.2 | 0.2 | 0.2 |
|  | 14. Polyoxyethylene sorbitol tetraoleate (40EO) | 0.5 | 0.5 | 0.5 | 0.5 | 0.5 | 0.5 | 0.5 | 0.5 |
|  | 15. Isopropyl lauroyl sarcosinate | — | — | — | 2.0 | — | — | — | — |
|  | 16. Cetyl 2-ethylhexanoate | 2.0 | 2.0 | 2.0 | — | 2.0 | 2.0 | 2.0 | 2.0 |
|  | 17. Dimethylpolysiloxane | 2.0 | 2.0 | 2.0 | 2.0 | 2.0 | 2.0 | 2.0 | 2.0 |
|  | 18. Dimethylcyclopolysiloxane | — | 2.0 | 2.0 | 2.0 | 2.0 | 2.0 | 2.0 | 2.0 |
|  | 19. Propylparaben | 0.1 | 0.1 | 0.1 | 0.1 | 0.1 | 0.1 | 0.1 | 0.1 |
| 20. Components B | 10% by weight aq. solution of sodium citrate | 2.0 | 3.0 | — | 2.0 | 2.0 | 2.0 | 2.0 | 2.0 |
|  | 10% by weight aq. solution of sodium chloride | — | — | — | — | 0.5 | — | — | — |
|  | 10% by weight aq. solution of magnesium chloride | — | — | 5.0 | 2.0 | — | 2.0 | 5.0 | 5.0 |
|  | 10% by weight aq. solution of sodium glycolate | — | 2.0 | — | — | — | — | — | — |
|  | 10% by weight sodium edetate | — | — | — | — | — | — | — | — |
| Powders | Poly(methyl methacrylate) resin | 2.0 | 2.0 | 2.0 | — | 2.0 | — | — | — |
|  | Silicone powder | — | — | — | 2.0 | — | 2.0 | 2.0 | 2.0 |
| Components C | *Glycyrrhiza glaba* extract | 1.0 | — | — | — | — | — | — | 1.0 |
|  | *Narcissus tazetta* extract | 1.0 | — | — | — | — | — | — | — |
|  | Peptide | 1.0 | — | — | — | — | — | — | — |
|  | Pearl extract | 1.0 | — | — | — | — | — | — | 1.0 |
| Total |  | 100 | 100 | 100 | 100 | 100 | 100 |  | 100 |

*1 "NIKKOL TXC" (trade name) of Nikko Chemicals Co. Ltd. was used.
Appearance: white-yellowish crystalline powder
Melting point: 131 to 135° C., Weight loss on drying: 1.0% or less (105° C., 2 hours)

Comparative Examples 4 to 7

Except that the compositions according to Table 8 were used, compositions for external use were prepared identically to Examples 17 to 24.

TABLE 8

| | | Unit: % by weight Comparative Example | | | |
|---|---|---|---|---|---|
| | Components | 4 | 5 | 6 | 7 |
| Water phase | 1. Purified water | Balance | Balance | Balance | Balance |
| | 2. Component A: cetyl tranexamate hydrochloride salt *1 | 0.5 | 2.0 | 3.0 | 5.0 |
| | 3. Pentyleneglycol | 2.5 | 2.5 | 2.5 | 2.5 |
| | 4. Polyoxyethylene methyl glucoside (10EO) | 2.0 | 2.0 | 2.0 | 2.5 |
| | 5. Raffinose | — | — | 1.0 | — |
| | 6. Chlorphenesin | — | — | 0.2 | — |
| | 7. Methylparaben | 0.2 | 0.2 | 0.2 | 0.2 |
| | 8. Guar gum | 0.2 | 0.1 | — | 0.2 |
| | 9. Hydroxyethyl cellulose | — | 0.1 | 0.2 | 0.2 |
| Oil phase | 10. Cetyl alcohol | 3.0 | 3.0 | 3.0 | 3.0 |
| | 11. Glyceryl monostearate | 0.2 | 0.2 | 0.1 | 0.2 |
| | 12. Sorbitan monostearate | 0.2 | 0.2 | 0.2 | 0.2 |
| | 13. Polyoxyethylene sorbitan monostearate (20EO) | 0.2 | 0.2 | 0.3 | 0.2 |
| | 14. Polyoxyethylene sorbitol tetraoleate (40EO) | 0.5 | 0.5 | 0.5 | 0.5 |
| | 15. Isopropyl lauroyl sarcosinate | — | — | 2.0 | — |
| | 16. Cetyl 2-ethylhexanoate | 2.0 | 2.0 | — | 2.0 |
| | 17. Dimethylpolysiloxane | 2.0 | 2.0 | 2.0 | 2.0 |
| | 18. Dimethylcyclo-polysiloxane | — | 2.0 | 2.0 | 2.0 |
| | 19. Propylparaben | 0.1 | 0.1 | 0.1 | 0.1 |
| 20. Components B | 10% by weight aq. solution of sodium citrate | — | — | — | — |
| | 10% by weight aq. solution of sodium chloride | — | — | — | — |
| | 10% by weight aq. solution of magnesium chloride | — | — | — | — |
| | 10% by weight aq. solution of sodium glycolate | — | — | — | — |
| | 10% by weight sodium edetate | — | — | — | — |
| Powders | Poly(methyl methacrylate) resin | 2.0 | 2.0 | — | — |
| | Silicone powder | — | — | 2.0 | 2.0 |
| Total | | 100 | 100 | 100 | 100 |

*1 "NIKKOL TXC" (trade name) of Nikko Chemicals Co. Ltd. was used.
Appearance: white - yellowish crystalline powder
Melting point: 131 to 135° C.,
Weight loss on drying: 1.0% or less (105° C., 2 hours)

[Evaluation of Stability on Examples 17 to 24 and Comparative Examples 4 to 7]

The conditions of the prepared compositions for external use of Examples 17 to 24 and Comparative Examples 4 to 7 were observed visually immediately after the preparation, after standing overnight after the preparation at room temperature (20 to 25° C.), and after standing for 2 weeks or 2 months after the preparation at 45° C. The conditions of the compositions for external use were evaluated according to the following rating scale. The results are shown in Table 9.

(Rating scale)

⊚: A uniform composition for external use was obtained immediately after preparation, and the uniform condition was kept over storage for 2 months at 45° C.;

○: A uniform composition for external use was obtained immediately after preparation, and the uniform condition was kept over storage for 2 weeks at 45° C.;

Δ: A uniform composition for external use was obtained immediately after preparation, but separation or aggregation was observed after storage for 2 weeks at 45° C.; and x: Layer or water separation was observed on the next day of the preparation, and therefore a uniform composition for external use was not obtained.

TABLE 9

| | Example | | | | | | | | Comparative Example | | | |
|---|---|---|---|---|---|---|---|---|---|---|---|---|
| | 17 | 18 | 19 | 20 | 21 | 22 | 23 | 24 | 4 | 5 | 6 | 7 |
| Stability | ○ | ⊚ | ○ | ⊚ | ⊚ | ⊚ | ⊚ | ⊚ | Δ | X | X | X |

As shown in Table 9, the compositions for external use according to Examples 17 to 24 were obtained in the state of a uniform dispersion with white turbid appearance. Especially in case a combination of sodium citrate and another salting-out agent was used, improved stability was recognized. In contrast, in cases of Comparative Examples 4 to 7, separation or aggregation was recognized, and the uniform dispersion state could not be maintained. Especially, in case the component A was added at 1.0% by weight or more, layer or water separation occurred within a day of the preparation of a composition for external use, and a composition in a uniform dispersion state for external use could not be afforded.

Examples 25 to 27

Compositions for external use were prepared as follows according to the compositions set forth in Table 10 (an O/W-type milky lotion).

1) The water phase components 1 to 10 were dissolved under stirring with heating at 85±5° C. (a water phase mixture 1).

2) The oil phase components 13 to 22 were dissolved under stirring with heating at 85±5° C. (an oil phase mixture).

3) Sodium citrate (Component 11) was added to the water phase mixture 1 kept at 85±5° C. with stirring (a water phase mixture 2). The water phase mixture 2 was in a transparent state by visual observation.

4) Magnesium sulfate (Component 12) was added to the water phase mixture 2 kept at 85±5° C. with stirring (a water phase mixture 3). The water phase mixture 3 clouded white, and cetyl tranexamate precipitated as fine particles.

5) The oil phase mixture kept at 85±5° C. was added to the water phase mixture 3 kept at 85±5° C. with stirring (an emulsified mixture).

6) Starting cooling of the emulsified mixture with stirring, and at 35±5° C. the components 23 to 26 were added in turn to obtain a milky lotion.

Although the components 11 and 12 were added in turn in the above examples, they may be added simultaneously.

TABLE 10

| | Components | Example 25 | Example 26 | Example 27 |
|---|---|---|---|---|
| Water phase | 1. Purified water | Balance | Balance | Balance |
| | 2. Component A: cetyl tranexamate *1 | 1.00 | 3.00 | 5.00 |
| | 3. Pentylene glycol | 3.00 | 3.00 | 3.00 |
| | 4. Polyoxyethylene methyl glucoside (10EO) | 2.00 | 2.00 | 2.00 |
| | 5. Raffinose | 1.00 | 1.00 | 1.00 |
| | 6. Glycerine | 5.00 | 4.00 | 4.00 |
| | 7. Capryl glycol | 0.25 | — | — |
| | 8. Methylparaben | — | 0.25 | 0.25 |
| | 9. Guar gum | 0.20 | 0.30 | 0.20 |
| | 10. Hydroxyethyl cellulose | 0.20 | 0.20 | 0.20 |
| 11. Sodium citrate | | 0.10 | 0.20 | 0.50 |
| 12. Magnesium sulfate | | 0.50 | 1.00 | 1.50 |
| Oil phase | 13. Cetyl alcohol | 1.5 | 2.00 | 2.0 |
| | 14. Glyceryl monostearate | 0.5 | — | 0.5 |
| | 15. Sorbitan monostearate | 1.0 | — | — |
| | 16. Polyoxyethylene sorbitan monostearate (20EO) | — | 0.5 | 1.0 |
| | 17. Polyoxyethylene sorbitol tetraoleate (40EO) | 0.50 | 0.50 | 0.50 |
| | 18. Isononyl isononanoate | 2.00 | 2.00 | 2.00 |
| | 19. Cetyl 2-ethylhexanoate | 2.00 | 2.00 | 2.00 |
| | 20. 2-Octyldodecyl myristate | 1.00 | 1.00 | 1.00 |
| | 21. Dimethylpolysiloxane | 4.00 | 4.00 | 4.00 |
| | 22. Silicone powder *2 | 2.00 | 1.00 | 1.00 |
| 23. Water-soluble polymers | Sodium hyaluronate (1% by weight aq. solution) | 5.00 | — | — |
| | *Polianthes tuberosa* polysaccharide (1% by weight aq. solution) *3 | — | 2.00 | — |
| | Xanthan gum (1% by weight aq. solution) | — | — | 2.00 |
| 24. Phenoxyethanol | | 0.30 | 0.30 | 0.30 |
| 25. Perfume | | 0.20 | 0.20 | 0.20 |
| 26. Active components | *Glycyrrhiza glabra* extract | 1.00 | 1.00 | 1.00 |
| | *Narcissus tazetta* extract | 1.00 | 1.00 | 1.00 |
| | Peptide | 1.00 | 1.00 | 1.00 |
| | Pearl extract | 1.00 | 1.00 | 1.00 |
| Total | | 100 | 100 | 100 |

*1 "NIKKOL TXC" (trade name) of Nikko Chemicals Co. Ltd. was used.
Appearance: white to yellowish crystalline powder
Melting point: 131 to 135° C.,
Weight loss on drying: 1.0% or less (105° C., 2 hours)
*2 "TOSPEARL 2000B" (trade name) of Momentive Performance Materials Japan LLC was used.
Appearance: spherical (average particle size 6.0 μm), fine white particles
*3 "SOFCARE TP-S" (trade name) of Kao Corporation was used.
Composition: *Polianthes tuberosa* polysaccharide 1%, ethanol and water
Appearance: colorless to yellowish, transparent to translucent, viscous liquid

[Evaluation of Stability on Milky Lotions According to Examples 25 to 27]

The obtained milky lotions were homogeneous immediately after the preparations. The homogeneous conditions could be maintained over 2-month storage at 45° C. with respect to all the obtained milky lotions.

Examples 28 to 30

Compositions for external use were prepared as follows according to the compositions set forth in Table 11 (a W/O-type cream).

1) The water phase components 1 to 8 were dissolved under stirring with heating at 85±5° C. (a water phase mixture 1).
2) The oil phase components 15 to 24 were mixed with stirring (an oil phase mixture).
3) Sodium citrate (Component 9) was added to the water phase mixture 1 kept at 85±5° C. with stirring (a water phase mixture 2). The water phase mixture 2 was in a transparent state by visual observation.
4) Magnesium sulfate (Component 10) was added to the water phase mixture 2 kept at 85±5° C. with stirring (a water phase mixture 3). The water phase mixture 3 clouded white, and cetyl tranexamate precipitated as fine particles.
5) The water phase mixture 3 was cooled with stirring to 35±5° C., to which the components 11 to 14 were added in turn with stirring (water phase mixture 4).
6) The water phase mixture 4 was added to the oil phase mixture with vigorous stirring to obtain a cream.

Although the components 9 and 10 were added in turn in the above examples, they may be added simultaneously.

TABLE 11

| | Components | Example 28 | Example 29 | Example 30 |
|---|---|---|---|---|
| Water phase | 1. Purified water | Balance | Balance | Balance |
| | 2. Component A: cetyl tranexamate *1 | 1.00 | 3.00 | 5.00 |
| | 3. Pentylene glycol | 2.00 | 2.00 | 2.00 |
| | 4. Polyoxyethylene methyl glucoside (10EO) | 2.00 | 2.00 | 2.00 |
| | 5. Raffinose | 1.00 | — | 2.00 |
| | 6. Glycerine | 8.00 | 8.00 | 5.00 |
| | 7. Methylparaben | 0.20 | 0.20 | 0.20 |
| | 8. Capryl glycol | 0.05 | — | — |
| 9. Sodium citrate | | 0.20 | 0.20 | 0.20 |
| 10. Magnesium sulfate | | 0.50 | 1.00 | 1.50 |
| 11. Ethanol | | 6.00 | 4.00 | 4.00 |
| 12. Phenoxyethanol | | 0.30 | 0.30 | 0.30 |
| 13. Perfume | | 0.20 | 0.20 | 0.20 |
| 14. Active components | *Glycyrrhiza glabra* extract | 1.00 | 1.00 | 1.00 |
| | *Narcissus tazetta* extract | 1.00 | 1.00 | 1.00 |
| | Peptide | 1.00 | 1.00 | 1.00 |
| | Pearl extract | 1.00 | 1.00 | 1.00 |
| Oil phase | 15. Silicone elastomer *2 | 4.00 | 4.00 | 4.00 |
| | 16. Isononyl isononanoate | 4.00 | 4.00 | 4.00 |
| | 17. Cetyl 2-ethylhexanoate | 4.00 | 4.00 | 4.00 |
| | 18. 2-Octyldodecyl myristate | 2.00 | 2.00 | 2.00 |
| | 19. Dimethylpolysiloxane | 4.00 | 4.00 | 4.00 |
| | 20. Silica dimethyl silylate | 0.25 | 0.25 | 0.50 |
| | 21. Silicone powder *3 | 2.00 | 2.00 | 2.00 |
| | 22. Silicone gel *4 | — | 6.00 | 6.00 |
| | 23. Polyether-modified silicone *5 | — | 0.50 | 0.50 |
| | 24. Protesil FN *6 | 4.00 | — | — |
| Total | | 100 | 100 | 100 |

*1 "NIKKOL TXC" (trade name) of Nikko Chemicals Co. Ltd. was used.
Appearance: white to yellowish crystalline powder
Melting point: 131 to 135° C.
Weight loss on drying: 1.0% or less (105° C., 2 hours)
*2 "DC 9041" (trade name) of Dow Corning Toray Co., Ltd. was used.
Components: dimethicone crosspolymer 16%, and Dimethylpolysiloxane (5 cs) 84%
Appearance: colorless to yellowish, transparent to translucent, viscous liquid
*3 "TOSPEARL 2000B" (trade name) of Momentive Performance Materials Japan LLC used.
Appearance: spherical white microbeads (average particle size 6.0 μm)
*4 "KSG-210" (trade name) of Shin-Etsu Chemical Co., Ltd. was used.
Components: (dimethicone/(PEG-10/15)) crosspolymer 24%, and Dimethylpolysiloxane (6 cs) 76%
Appearance: colorless translucent paste
*5 "KF-6028" (trade name) of Shin-Etsu Chemical Co., Ltd. was used.
Component: PEG-9 polydimethylsiloxyethyl dimethicone
Appearance: colorless, translucent, viscous liquid
*6 "PROTESIL FN" (trade name) of Seiwa Kasei Co., Ltd. was used.
Components: (hydrolyzed silk/PG-propyl methylsilanediol)crosspolymer, cyclopentasiloxane, and water

[Evaluation of Stability on Creams According to Examples 28 to 30]

The obtained creams were homogeneous immediately after the preparations. The homogeneous conditions could be maintained over 2-month storage at 45° C. with respect to all the obtained creams.

INDUSTRIAL APPLICABILITY

The composition for external use of the present invention enjoys suppressed sticky or oily feeling, and therefore is, as a composition for external use providing comfortable feel of use, favorably applicable to drugs, quasi drugs and cosmetics. The composition for external use of the present invention can be utilized in various formulation and product forms.

The invention claimed is:

1. A method for producing a composition for external use, the method comprising the steps of:
   a) dissolving a physiologically acceptable salt of a tranexamate in a solvent,
   b) adding at least one salting-out agent into the obtained solution and precipitating the salt as crystals of fine particles having an average particle size of 0.01 μm to 100 μm, and
   c) dispersing the precipitated salt in a composition for external use.

2. The method according to claim 1, wherein the tranexamate is represented by formula (1),

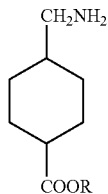

(1)

wherein R represents a C1 to C22 linear saturated hydrocarbon group, a C2 to C22 linear unsaturated hydrocarbon group, or a C3 to C22 branched, saturated or unsaturated, hydrocarbon group, which may be substituted by at least one substituent selected from hydroxy and amino groups.

3. The method according to claim 1, wherein the physiologically acceptable salt of a tranexamate is cetyl tranexamate hydrochloride salt.

4. The method according to claim 1, wherein the particles have an average particle size of 0.05 μm to 50.0 μm.

5. The method according to claim 1, wherein the solvent is selected from the group consisting of water, a lower alcohol, a polyhydric alcohol, ethers, esters, ketones, and a mixture thereof.

6. The method according to claim 1, wherein said at least one salting-out agent is selected from the group consisting of a citrate, an edetate, a glycolate, a phosphate, a hydrochloride, a sulfate, an acetate, a tartrate, a bromate, an oxalate, a lactate, a carbonate and a chloride salt.

7. The method according to claim 1, wherein the concentration of tranexamate salt dissolved in the solvent is 1.0 to 5.0% by weight of the solution.

8. The method according to claim 1, wherein the concentration of salting-out agent is 0.2 to 1.0% by weight of the solution.

9. The method according to claim 1, wherein the particles have an average particle size of 0.1 μm to 10.0 μm.

10. The method according to claim 1, wherein the tranexamate salt is dissolved in the solvent at a temperature of 50° to 120° C.

11. The method according to claim 1, wherein the tranexamate salt is dissolved in the solvent at a temperature of 80° C. to 90° C.

* * * * *